(12) United States Patent
Brandon et al.

(10) Patent No.: US 11,589,978 B2
(45) Date of Patent: Feb. 28, 2023

(54) METHOD AND APPARATUS FOR TESTING BREAST IMPLANTS

(71) Applicants: Harold J. Brandon, St. Louis, MO (US); Dwight D. Back, Satellite Beach, FL (US)

(72) Inventors: Harold J. Brandon, St. Louis, MO (US); Dwight D. Back, Satellite Beach, FL (US)

( * ) Notice: Subject to any disclaimer, the term of this patent is extended or adjusted under 35 U.S.C. 154(b) by 535 days.

(21) Appl. No.: 16/865,342

(22) Filed: May 2, 2020

(65) Prior Publication Data

US 2020/0345477 A1 Nov. 5, 2020

Related U.S. Application Data

(60) Provisional application No. 62/920,560, filed on May 3, 2019.

(51) Int. Cl.
*A61F 2/12* (2006.01)

(52) U.S. Cl.
CPC ........ *A61F 2/12* (2013.01); *A61F 2230/0004* (2013.01); *A61F 2230/0063* (2013.01); *A61F 2240/008* (2013.01); *A61F 2250/0014* (2013.01)

(58) Field of Classification Search
CPC ................ A61F 2/12; A61F 2230/0004; A61F 2230/0063; A61F 2240/008; A61F 2250/0014

See application file for complete search history.

(56) References Cited

U.S. PATENT DOCUMENTS

| | | | | |
|---|---|---|---|---|
| 6,005,911 | A  * | 12/1999 | Cheung | A61B 6/502 |
| | | | | 378/98.8 |
| 6,416,218 | B1 * | 7/2002 | Cheung | A61B 6/548 |
| | | | | 378/207 |
| 10,379,106 | B2 * | 8/2019 | Gasik | G01N 33/5375 |
| 2019/0025286 | A1 * | 1/2019 | Gasik | G01N 33/5008 |
| 2020/0345477 | A1 * | 11/2020 | Brandon | A61F 2/12 |
| 2022/0379036 | A1 * | 12/2022 | Moeller | A61M 5/20 |

FOREIGN PATENT DOCUMENTS

WO    WO-2021191897 A1 *  9/2021  ............. A61L 27/24

OTHER PUBLICATIONS

New Evaluation Procedure for Multi-Dimensional Mechanical Strains and Tangent Moduli of Breast Implants, Bioengineering 2019, 6, 43, Publication date May 12, 2019.

* cited by examiner

*Primary Examiner* — Suzette J Gherbi

(57) ABSTRACT

This invention provides a method for determining breast implant geometric properties, engineering stresses, engineering strains and engineering moduli; directly and quickly, using a load frame apparatus. More generally the invention provides a method for determining geometric properties and engineering mechanical properties of any elastomeric device, using a load frame apparatus. Engineering stress and engineering strain properties of breast implants are critical to their safety and durability. The geometric properties of breast implants undergoing compression also relates to the shape stability of breast implants, which may also be related to clinical outcomes such as capsular contracture and other untoward outcomes involving a breast capsule, such as Anaplastic Large Cell Lymphoma (ALCL), double capsule formation, seroma formation and associated breast implant illness (BII).

20 Claims, 9 Drawing Sheets

METHOD AND APPARATUS FOR TESTING BREAST IMPLANTS

CROSS-REFERENCE TO RELATED APPLICATIONS

Provisional patent application 62/920,560, having a filing or 371(c) date of May 3, 2019.

BACKGROUND OF THE INVENTION

Field of the Invention

The field of this invention relates generally to test methods employed to characterize the geometry and engineering mechanical properties of breast prostheses, or breast implants, and more generally, any elastomeric device. More specifically, the field of this invention relates to engineering mechanical properties, including, but not limited to, engineering stresses, engineering strains, engineering moduli, pressure, and ultimate strength of breast implants when a breast implant is subjected to compressive forces. And, more specifically, this invention relates to a quick and simplified method for determining breast implant geometric and engineering mechanical properties using only load-displacement data commonly measured using a load frame apparatus, along with the breast implant's volume and shell thickness.

Description of Related Art

Breast implants are regulated medical devices. Regulatory bodies such as the FDA require testing of these medical devices to prove that they are safe and durable.

Saline-filled and silicone gel-filled breast implants that are marketed today have undergone extensive mechanical testing to demonstrate strength and durability. Breast implant manufacturers have followed the recommendations provided by medical device regulatory bodies which require specific types of mechanical tests and expected strength and durability requirements of silicone shells and the finished product. Many of the current mechanical evaluations utilize ASTM and ISO standards. Mechanical testing that replicates clinical conditions is the goal of these experimental procedures, but this is difficult to achieve in the laboratory. Instead, breast implant manufacturers have used conventional experimental techniques that can be performed in any well-equipped mechanical testing laboratory.

Current routine breast implant testing includes tensile strength, ultimate elongation, tear resistance, joint testing, cyclic fatigue testing, ultimate strength tests, and valve competency (for saline-filled breast implants). These mechanical tests have not exactly simulated the in vivo environment. A test methodology that simulates in vivo conditions would be the desired procedure to evaluate the geometric and engineering mechanical properties of breast implants, but this is difficult to achieve in the laboratory.

Compression testing between two parallel plates, or platens, in air or saline solution, has been used previously by breast implant manufacturers for cyclic fatigue and ultimate strength testing. Flat plate compression testing has been used to provide breast implant cyclic fatigue failure characteristics, data for fatigue lifetime predictions, ultimate strength, and morphological features of fatigue failure.

To evaluate the stress and strain properties of breast implants when subjected to a compressive load, current methods entail complex and time-intensive finite element or finite difference modeling, and are not readily applied to assess the safety and durability of breast implants.

Hence, it is highly desirable to have a simplified method for evaluating the geometric and engineering mechanical properties of breast implants. This simplified method is needed not only to assess the safety and durability of current breast implants, but also to facilitate the design of safer and more durable future breast implants.

The geometric and engineering mechanical properties of breast implants subjected to compressive forces may also relate clinical outcomes such as capsular contracture, and other untoward outcomes involving a breast capsule, such as Anaplastic Large Cell Lymphoma (ALCL), double capsule formation, seroma formation and associated breast implant illness (BII), and in vivo rupture. Consequently, a simplified and easily implemented means to assess these breast implant properties could aid in understanding their relationship to current clinical outcomes, and in designing breast implants which will have better clinical outcomes.

Objects of the Invention

This invention has several objects to address the deficiencies of current breast implant testing methods:

An object of this invention is to provide a simplified and quick means to determine breast implant geometries, and changes in geometry, entirely from common load-displacement data measured using a load frame apparatus and the breast implant's volume and shell thickness.

An object of this invention is to provide the means to determine the various engineering mechanical properties (e.g., engineering stresses, engineering strains, and engineering moduli) of breast implants entirely from common load-displacement data measured using a load frame apparatus and the breast implant's volume and shell thickness.

Another object of this invention is to provide a simplified method that uses a quasi-equilibrium assumption for an implant's geometric state, which allows a breast implant's geometric properties and engineering mechanical properties to be determined by a load frame apparatus implementing a dynamic test program. This eliminates the need for time-intensive static load frame apparatus testing, whereby a load would have to be stepwise applied, followed at each step with manual measurements of an implant's geometry.

Another object of this invention is to provide the breast implant industry a means to assess the impact of breast implant design changes, including but not limited to, filler material, shell thickness, breast implant fill volume, and breast implant shape, on the safety and durability of a breast implant.

Yet another object of this invention is to provide the means to comprehensively evaluate the geometric and engineering mechanical properties of breast implants during ultimate strength testing and cyclic fatigue testing using load and displacement data from a load frame apparatus.

Another object of this invention is to provide breast implant manufacturers a means to quickly determine a comprehensive series of breast implant properties during product design, product development, production, or quality assurance.

Yet another object of this invention is to provide a method to characterize the geometry and engineering mechanical properties of a variety of breast implant designs including, but not limited to, multi-lumen breast implants and anatomically shaped breast implants.

An object of this invention is also to provide a simplified and quick means to determine geometric and engineering mechanical properties of elastomeric devices other than breast implants.

BRIEF SUMMARY OF THE INVENTION

This invention relates to quickly determining the geometry and engineering mechanical properties (e.g., engineering stresses, engineering strains and engineering moduli) of breast implants, in their implanted or implantable form, using only the load-displacement data that is typically generated from a load frame apparatus during mechanical testing procedures. When referring to a breast implant in this invention disclosure, it is understood that the breast implant is in its implanted or implantable form. A breast implant will comprise at least one shell-enclosed lumen, and breast implants comprised of more than one shell-enclosed lumen may also be referred to as a multi-lumen breast implant.

It was discovered that a geometry state of quasi-equilibrium could be assumed when breast implants are dynamically tested in a load frame apparatus, thereby eliminating the need for time-intensive manual measurements and data recording during load frame testing after each stepwise load change is applied to a breast implant. A quasi-equilibrium process is one in which the deviation from equilibrium is infinitesimal, and all the states the breast implant passes through during the transient, or dynamic, process may be considered equilibrium states. Therefore, this assumption constrains all breast implant properties to be constants for every instantaneous compression load during the automatic, or dynamic, load-displacement test process or dynamic load program.

This invention simplifies the determination of crucial breast implant properties that relate directly to the safety and durability of breast implants or other elastomeric devices. The invention also provides a quick test, taking only minutes, to ascertain a broad spectrum of geometric and engineering mechanical properties of a breast implant.

Using this invention, load (or force) measurements are acquired as a function of platen displacement, or plate spacing, in a load frame apparatus. These measured load-displacement parameters can be acquired automatically with a data acquisition system or recorded manually. With this load-displacement data, all geometric properties and engineering mechanical properties of the breast implant can be calculated knowing the breast implant volume and shell thickness if the breast implant is comprised of a shell enclosing a fluid such a saline solution or elastomeric filler such as a silicone gel.

The examples and description in this disclosure primarily reference a breast implant, however, it is understood that this invention can also be applied to other elastomeric devices for which the geometry of the elastomeric device can be accurately modeled in terms of geometric shapes or composites thereof that can be derived mathematically using plate spacing data from a load frame apparatus and the device's volume. An elastomeric device is understood to be any device comprised of an elastomeric material that encloses a lumen filled with a fluid or gel. In the context of this invention and engineering terminology, the term fluid is understood to be any gaseous or liquid material. An elastomeric device may also be monolithic or contiguous, with no enclosed fluids or gels.

This invention has been shown to produce accurate modeling of breast implant geometry, and therefore accurate engineering mechanical properties (i.e., stresses, strains and moduli) that are a function of the measured load and breast implant geometry.

This invention provides the means to quickly determine breast implant geometry using only the plate spacing data and breast implant volume, utilizing the novel approach of modeling a compressed breast implant as a combination of a flattened cylinder and the outer-half of a torus. The area of contact of the load frame platens with the breast implant can also be determined by this invention.

Given the geometric properties of a breast implant undergoing compression, various engineering mechanical properties can then be determined from the measured load profile. In particular, the internal pressure of the breast implant can be calculated from the load and platen contact area, the circumferential stress can be calculated from the load, shell thickness and breast implant geometry, and multi-dimensional strains can be calculated using the breast implant geometry.

Engineering stresses that can be determined by this invention include, but are not limited to, planform, circumferential and normal.

Engineering strains that can be determined using this invention include, but are not limited to, projection, diametric and areal, which refer to changes in breast implant height, diameter and surface area, respectively. Collectively, these engineering strains may be referred to as multi-dimensional strains. The breast implant multi-dimensional strains and associated breast implant shape change due to compression is a mechanical property that has not been previously evaluated for breast implants. Breast implant strain is directly related to breast implant shape change.

Engineering moduli, or the ratio of stress to strain, can also be calculated by this invention for a breast implant from only the load and displacement data and knowing the breast implant volume and shell thickness. Engineering moduli are important properties of breast implants which describe the compressibility, firmness and shape stability of a breast implant, which are crucial properties related to the safety and durability of breast implants.

BRIEF DESCRIPTION OF SYMBOLS & NUMBERS

Figure 1:
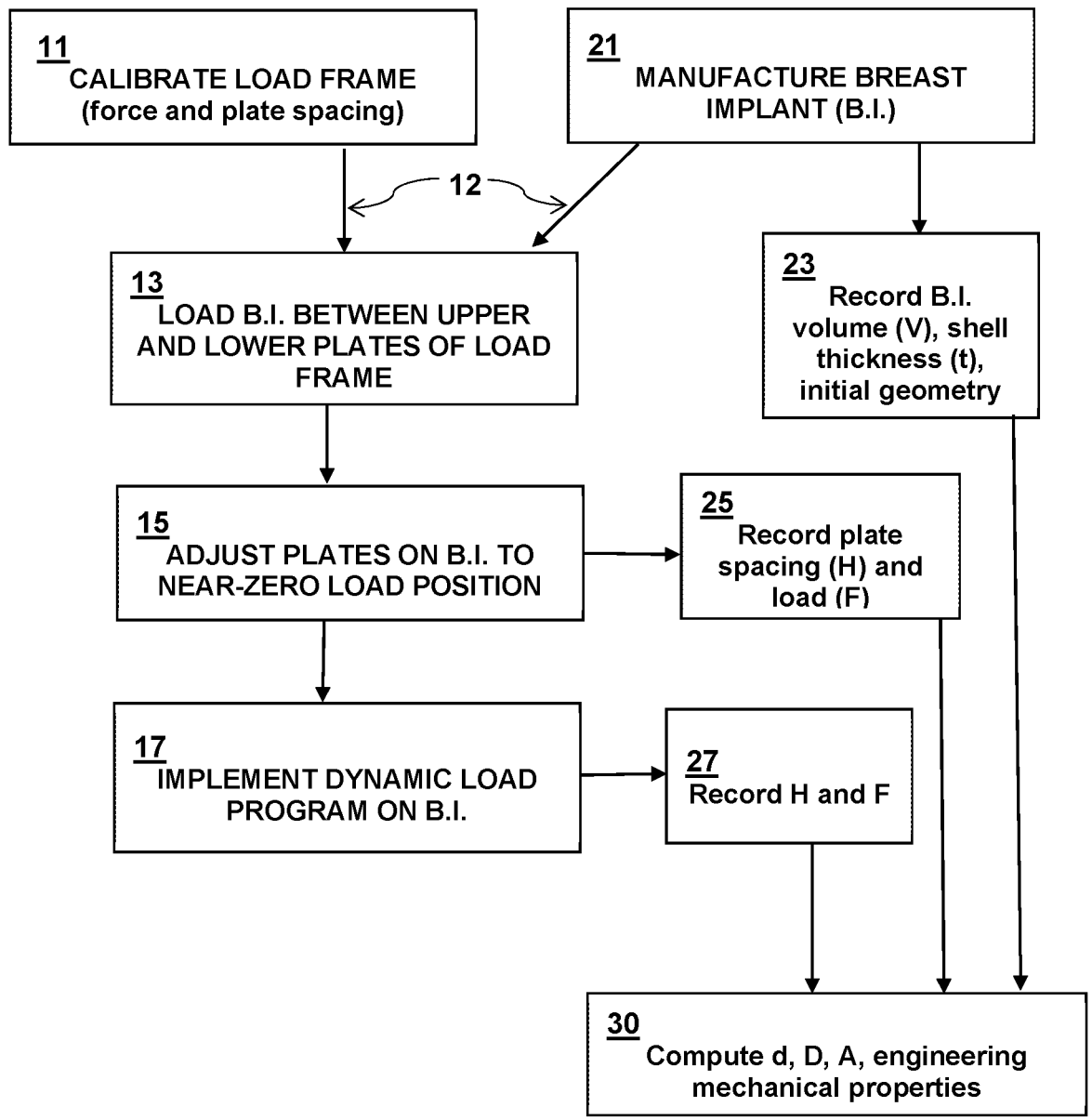
FIG. 1 summarizes the process or protocol steps for determining engineering mechanical properties (i.e., engineering stresses, engineering strains and engineering moduli) using a load frame apparatus.

11—Process or protocol step of calibrating the load frame apparatus.

12—Process or protocol step of optionally lubricating the load frame plates, optionally lubricating the breast implant, or optionally lubricating both.

13—Process or protocol step of loading a breast implant between two platens comprising the load frame apparatus.

15—Process or protocol step of adjusting the spacing between the plates of the load frame apparatus so that the load on the breast implant is near zero. This is the initial state before commencing the testing process of this invention.

17—Process or protocol step of implementing a dynamic load program with the load frame apparatus.

21—Process or protocol step of manufacturing a breast implant to be tested by the method of this invention.

23—Process or protocol step of recording the breast implant volume, shell thickness, and initial breast implant geometry.

25—Process or protocol step of recording the plate spacing and load applied to an implant in its initial near-zero load state.

27—Process or protocol step of recording the plate spacing and applied load to a breast implant while the dynamic load program is being implemented by the load frame apparatus.

30—Process or protocol step of computing the geometry and engineering mechanical properties (i.e., engineering stresses, engineering strains and engineering moduli) of a breast implant subjected to dynamic compressive load using only load frame apparatus dynamic plate spacing, load frame apparatus dynamic load, breast implant volume and breast implant shell thickness.

100—Breast implant or other elastomeric device (cross section view).

101—Flattened cylinder component of composite geometric model for a compressed breast implant (cross section view).

102—Outer-half of torus component of composite geometric model for a compressed breast implant (cross section view).

201—Upper platen, or plate, of a load frame apparatus.

202—Lower platen, or plate, of a load frame apparatus.

A—Surface area of a breast implant or elastomeric device. $A_o$ refers to the initial implant surface area at near-zero load or before a load has been applied.

$A_x$—Area "x" used for computing a stress. (Example: $A_p$ is the planform area $\pi D^2/4$).

B.I.—Breast implant.

D—Diameter of a breast implant or elastomeric device. $D_o$ refers to the initial implant diameter at near-zero load or before a compressive load has been applied.

d—Contact diameter of a breast implant or elastomeric device with the upper and lower platens of a load frame apparatus.

$e_g$—Engineering strain based on geometric property g.

$E_{xg}$—Engineering modulus based on stress $S_x$ and geometric property g.

F—Force or load. In the context of this invention, the force or load is compressive to the elastomeric device or breast implant being tested.

g—Generalized geometric property of breast implant or elastomeric device, e.g., H, D and A.

$g_o$—Geometric property at near-zero or minimal compressive load.

H—Plate spacing, or distance between the upper and lower platens, or plates, of a load frame apparatus. Also may be referred to as platen displacement, or simply displacement. This also refers to the breast implant height or elastomeric device height, or breast implant projection or elastomeric device projection, in the load frame apparatus during load frame testing. $H_o$ refers to the initial breast implant or elastomeric device height, or projection, at near-zero load or before a load has been applied.

M—Mass of breast implant.

P—Pressure.

$\rho$—Density of breast implant.

$S_x$—Engineering stress based on area A.

t—Shell thickness of a breast implant or elastomeric device comprised of a shell enclosing a fluid or gel.

V—Volume of breast implant or elastomeric device. When this invention is applied to a breast implant, volume V can represent the total volume of the elastomeric device or breast implant including all shell-enclosed lumens comprising the elastomeric device or breast implant if the elastomeric device or breast implant is a multi-lumen elastomeric device or breast implant. This invention can also be applied to the individual shell-enclosed lumens of the multi-lumen elastomeric device or breast implant, in which case there can be a volume V for each of the shell-enclosed lumens of the multi-lumen elastomeric device or breast implant.

DETAILED DESCRIPTION OF THE INVENTION

This invention relates to quickly determining the geometry and engineering mechanical properties of breast implants undergoing dynamic compression using only load-displacement data that are typically measured and recorded by a load frame apparatus. Breast implants are typically comprised of one or more lumens enclosed by a shell, with the one or more lumens filled with a fluid or gel. This invention simplifies the determination of crucial breast implant geometric properties and engineering mechanical properties that relate directly to the safety and durability of breast implants.

A load frame apparatus typically comprises an upper plate and a lower plate that have surfaces that are parallel to one another, whereby at least one of the platens, or plates, is controllably movable relative to the other thereby controlling the plate spacing and compression on a device disposed between the upper plate and lower plate. The separation distance between the two platens, or plates, is referred to as the plate spacing, or displacement, (H). The plate spacing can be programmably controlled to continuously (i.e., dynamically) or discretely (i.e., stepwise) decrease or increase with a crosshead speed, thus increasing or decreasing the compressive load on the object placed between the upper and lower platens. Discretely controlled plate spacing allows for static or manual measurements of breast implant geometric properties and plate spacing as it is subjected to a stepwise-applied load, whereas continuously or dynamically controlled plate spacing provides for dynamic measurements and automatic recording of breast implant geometric properties as it is subjected to a dynamic compressive load.

In a preferred embodiment, this invention provides a method for utilizing dynamic measurements and appropriate geometry models of the compressed breast implant to quickly determine geometric properties and engineering mechanical properties of a breast implant without the need for complex and time-intensive calculations such as finite element or finite difference modeling, or time-intensive manual (or static) measurements.

The dynamic load program may comprise an increasing compressive load (decreasing plate spacing), an oscillatory compressive load having a frequency, a decreasing compressive load (increasing plate spacing), or any combinational sequence thereof. A load cell integrated into the load frame apparatus provides accurate measurement of force F, or load, exerted on an object disposed between the upper and lower platens, or plates. State-of-the-art load frames will allow plate spacing and load measurements to be recorded digitally as a function of time according to a prescribed data acquisition sampling rate.

FIG. 1 summarizes the process or protocol steps comprising the test method of this invention whereby a load frame apparatus is used to compute the engineering mechanical properties (i.e., engineering stresses, engineering strains and engineering moduli) of a breast implant. The terminology such as crosshead speed, load frame, load, displacement, platen spacing, and platens (or plates) used to describe the invention's method of FIG. 1 and throughout this invention disclosure is terminology known by, and used by, those skilled in the art of mechanical testing. The load frame is first calibrated 11. A breast implant is manufactured 21 and is loaded into the load frame apparatus and disposed between the two plates 13 of a calibrated load frame. Preferably, and prior to loading the breast implant between the platens, the breast implant volume V, shell thickness t, and initial implant geometry (e.g., $D_o$, $A_o$, and $H_o$), should be recorded 23. However, the volume V and shell thickness t may also be recorded after completion of load program 17 when the breast implant has been removed from the load frame apparatus after completion of the test. The plate spacing H is then adjusted to a starting point 15, or initial state, for the testing so that both plates form an area of contact with the breast implant with minimal or near-zero load imparted on the breast implant. The plate spacing and near-zero initial compressive load is recorded 25. This type of initial state adjustment is commonly practiced by those skilled in the art of mechanical testing. The interface, or area of contact, between the platens and the breast implant, may be first optionally lubricated with a layer of lubricant as indicated by 12. To lubricate the interface, lubricant may be applied to the breast implant, load frame apparatus platens, or both. The lubricant must be compatible with the material of the breast implant to avoid alteration of the material properties of the breast implant during the test. Although the lubrication step of 12 is optional, it is a preferred embodiment of this invention to test breast implants both with lubrication and without lubrication. Examples of lubricants include, but are not limited to, aqueous solutions and silicone oils. A dynamic load program is then implemented 17 on the breast implant, whereby a compressive load is applied dynamically to the breast implant by dynamically changing the displacement (or plate spacing) between the upper plate and lower plate. The rate of change in displacement (or plate spacing) between the upper plate and lower plate in the field of mechanical testing is characterized as having a crosshead speed. In most load frame apparatus, this is equivalent to the rate or speed at which the upper plate moves relative to a stationary lower plate. The dynamically changing plate spacing (or displacement) and load are then recorded 27 during implementation of the dynamic load program 17. The dynamic plate spacing and dynamic compressive load are preferably automatically recorded using a data acquisition system integrated with the load frame apparatus. The implemented load program 17 may comprise an increasing compressive load (decreasing plate spacing), an oscillatory compressive load, a decreasing compressive load, or any combinational sequence thereof. The plate spacing H and load F are preferably recorded automatically by a data acquisition and storage system at a sampling rate, and then used along with the known constant breast implant's volume V and shell thickness t to compute the breast implant's geometry (e.g., contact diameter d of breast implant with the upper and lower plates, breast implant diameter D, and breast implant surface area A) and engineering mechanical properties (i.e., engineering stresses, engineering strains and engineering moduli) of the breast implant 30. Software may also be integrated into the data acquisition system of the load frame apparatus which provides a quasi-equilibrium geometric model for the implant, and converts the load-displacement raw data to implant geometry and engineering mechanical properties for digital or graphical display.

Using this invention, the load F (or force) measurements are acquired as a function of breast implant height or plate spacing H in a load frame apparatus as the plate spacing is dynamically changed. Breast implants generally have a height of about 10 centimeters (cm) or less; and with preferred load frame crosshead speeds of about 2.5 centimeters/minute (cm/min) to about 50 cm/min, the time to perform a test run can be very quick. With the load F and plate spacing H data, all breast implant geometric properties and engineering mechanical properties can be calculated knowing the constant breast implant volume V and shell thickness t of the breast implant shell, or enclosure. The breast implant volume V is typically provided by the breast implant manufacturer; however, a breast implant's volume V can be easily determined from the breast implant's mass M and the density p of the material(s) comprising the breast implant using the formula V=M/p. Since the method of this invention may only take a few minutes, and calculations from the data can be automated by computer program or spreadsheet, a full description of breast implant geometry and engineering mechanical properties can be obtained very quickly.

Figure 2:
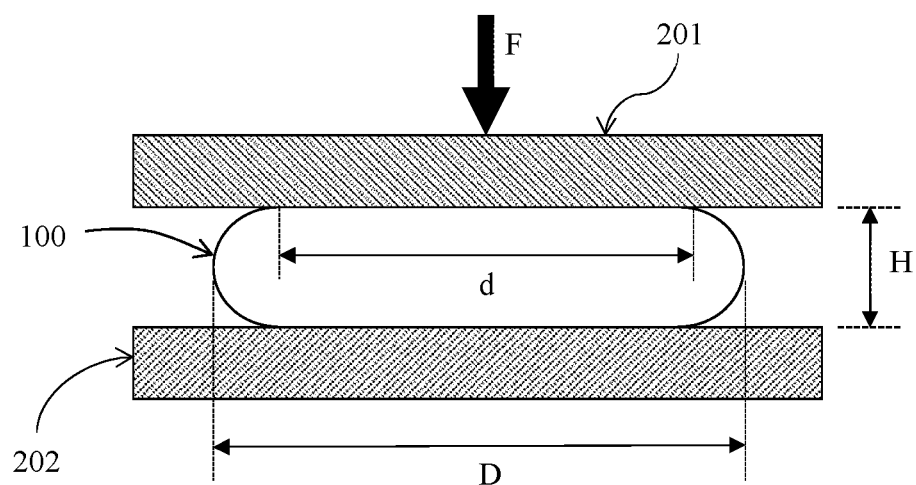
FIG. 2 illustrates the geometric descriptors for a breast implant undergoing compression in a load frame apparatus.

FIG. 2 is a drawing of a breast implant undergoing compression in a load frame apparatus. The upper platen 201 and lower platen 202 of a load frame apparatus contact the breast implant 100 with a diameter d. The breast implant also has a diameter D, which is the distance between the outer edges of the breast implant, and the distance between the upper platen 201 and lower platen 202 is H.

Figure 3:
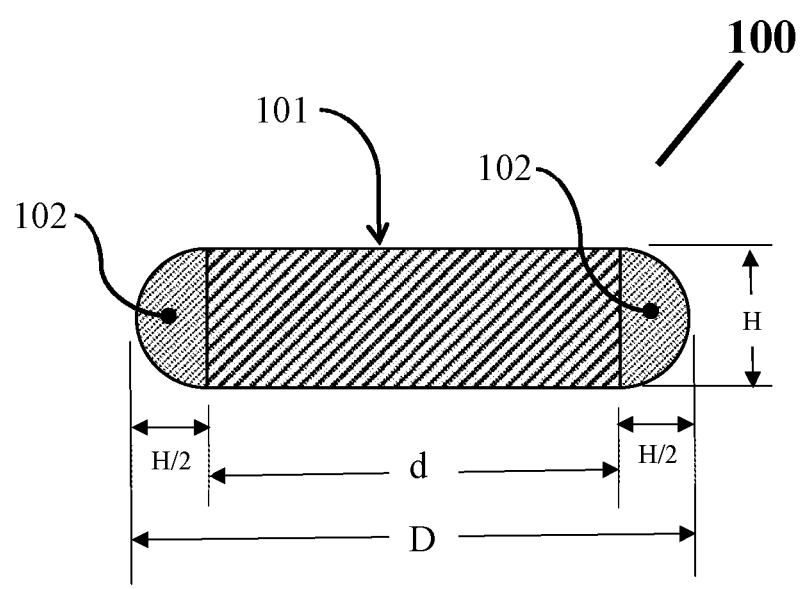
FIG. 3 illustrates the geometric components comprising the flattened cylinder and outer-half of a torus composite geometric model for a compressed breast implant (cross section view).

Referring to FIG. 3, it was discovered that a composite geometric model for a flattened cylinder 101 and the outer-half of a torus 102 accurately represents the geometry of a compressed breast implant. FIG. 3 also shows the dimensions d, D, and H which describe the geometry of the flattened cylinder and torus components. The volume V of this composite geometric model is given by:

$$V = \text{(volume cylinder)} + \text{(volume outer} - \text{half of torus)}, \quad (1)$$

$$V = \frac{\pi d^2 H}{4} + 2\pi\left(\frac{2H}{3\pi} + \frac{d}{2}\right)\frac{\pi H^2}{8}$$

where V is the breast implant volume, H is the plate spacing or breast implant height, and d is the diameter of contact of the breast implant with the upper platen 201 and lower platen 202. The volume V of Equation 1 can be the total breast implant volume, including the volume of all shell-enclosed lumens if the breast implant is comprised of multi-lumens. For a multi-lumen breast implant, an equation such as Equation 1 may also represent the shell-enclosed lumen volume of each individual shell-enclosed lumen of the multi-lumen breast implant if each shell-enclosed lumen of the multi-lumen breast implant are to be analyzed separately using the method of this invention.

Equation 1 can be solved for the breast implant-platen contact diameter d as $$d = \frac{1}{2}\left(-\frac{\pi H}{2} + \sqrt{\frac{16}{\pi}\frac{V}{H} + \left(\frac{\pi^2}{4} - \frac{8}{3}\right)H^2}\right) \quad (2)$$

Further, it was discovered that the outer curved perimeter surface of a breast implant undergoing compression can be accurately represented geometrically as a semi-circle having a diameter equal to H, which also corresponds to the diameter of the outer half of the torus. Equation 2 for breast implant-platen contact diameter d can then be simplified to an equation for the breast implant diameter D that is entirely a function of plate spacing H and the known constant breast implant volume V:

$$D = H + d \quad (3)$$

$$D = H + \frac{1}{2}\left(-\frac{\pi}{2}H + \sqrt{\frac{16}{\pi}\frac{V}{H} + \left(\frac{\pi^2}{4} - \frac{8}{3}\right)H^2}\right) \quad (4)$$

The same geometric assumption can also be used by this method to accurately calculate the surface area of a breast implant. Since it was discovered that a compressed breast implant can be accurately modeled as a composite of a flattened cylinder and outer-half of a torus, the surface area is:

$$A = \text{(area cylinder faces)} + \text{(area outer} - \text{half of torus)}, \quad (5)$$

$$A = \frac{\pi d^2}{2} + \frac{\pi^2 dH}{2} + \pi H^2,$$

$$A = \frac{\pi}{2}D^2 + \left(\frac{\pi^2}{2} + \pi\right)DH + \left(\frac{3\pi}{2} - \frac{\pi^2}{2}\right)H^2$$

Where A is the surface area of the breast implant. Since D is a function of plate spacing H and implant volume V by Equation 4, the surface area A can be calculated entirely from the load (F)-plate spacing (H) data and the known breast implant volume V.

Hence, using this invention's geometric model as a quasi-equilibrium state for a breast implant subjected to a dynamic compressive load, the breast implant geometry (e.g., diameter D, diameter d, and surface area A) can be computed entirely from the dynamic plate spacing H data and the known constant breast implant volume V.

Engineering stresses can also be calculated from the measured load F, shell thickness t and breast implant geometry, where the breast implant geometry is directly derived from the dynamic load frame apparatus load-displacement data and a quasi-equilibrium assumption for implant geometry as described in the preceding paragraphs and Equations 1-5. Engineering stresses are forces divided by an area. For a breast implant, the force is the applied compressive load, and various areas ($A_x$) can be used including, but not limited to, $\pi d^2/4$, $\pi d^2/4$, and $\pi Dt$. The general equation for computing various engineering stress by this method is:

$$S_x = \text{Stress} = F/A_x \quad (6)$$

Where $S_x$ denotes a stress S based on area $A_x$. The area $A_x$ used to compute a stress can be the planform area $\pi D^2/4$, shell cross section area $\pi Dt$, platen contact area $\pi d^2/4$, or some other area. Other more complex formulas for stress, depending on whether the compressed breast implant is best described as thin-walled or thick-walled are known by those skilled in the art, and are functions of geometric properties of the breast implant. For example, the maximum stress at the outer perimeter of a compressed breast implant can be derived as:

$$\text{Stress} = \frac{F(D^2 - d^2)}{\pi t D d^2} \quad (7)$$

This stress can also be calculated using only load (F)-displacement (H) data, since d and D are both functions of H per Equations 2 and 4, and the known and easily measured breast implant shell thickness t.

The breast implant internal pressure may be defined as a normal stress, whereby the area $A_x$ is the breast implant-platen contact area $\pi d^2/4$:

$$P = \text{Pressure} = F/(\pi d^2/4) \quad (8)$$

Engineering strain can be calculated using the breast implant geometry, which is entirely a function of the plate spacing H and known implant volume V using the method of this invention. Engineering strain is defined by the change is a geometric property relative to the initial geometric property value ($\Delta g = g - g_o$) divided by the initial geometric property $g_o$, where the geometric property g includes, but is not limited to, breast implant diameter D, plate spacing or breast implant height H, and breast implant surface area A. The general equation for engineering strain is:

$$\text{Strain} = e_g = \frac{g - g_o}{g_o} \quad (9)$$

Where $g_o$ is the initial geometric property g of the breast implant prior to applying a compressive load F. The strain associated with the height of the breast implant, diameter of the breast implant, and surface area of a breast implant are also referred to as projection, diametric and areal strain, respectively. This invention provides the means to determine the geometric properties g from the plate spacing measurements acquired using a load frame apparatus.

This method also provides the means to determine engineering moduli from load-displacement data. Engineering moduli are generally defined as the ratio of a stress to a strain.

$$\text{Modulus} = E_{xg} = \Delta S_x / \Delta e_g \qquad (10)$$

Where $\Delta S_x$ is the change in stress based on area $A_x$ and $\Delta e_g$ is the change in strain for geometric property g over a defined segment of the stress-strain curve. Typically, an engineering modulus is defined for the linear portion of the stress-strain curve where $S_x$ and $e_g$ approach zero. However, a tangent modulus can also be calculated over any portion of the stress-strain curve as the slope of the curve.

First Invention Embodiment

Figure 4:
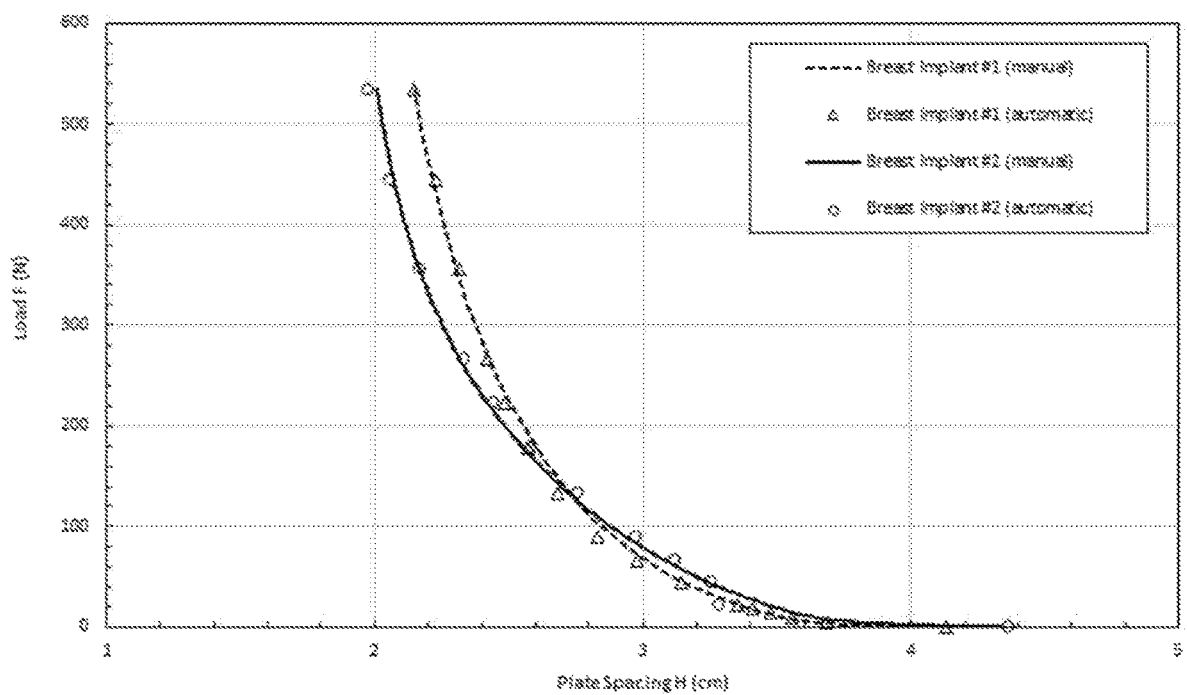
FIG. 4 compares load (F)-plate spacing (H) for manual (static) measurements to automatic (dynamic) compression testing of two breast implants.

FIG. 4 illustrates load (F)-displacement (H) measurements for two breast implants. The load frame crosshead speed used for the testing of FIG. 4 was 25.4 cm/min, making the test run time for the data shown in FIG. 4 on the order of a few minutes. In FIG. 4, Breast implant #1 is a saline-filled dual-lumen breast implant in which the breast implant-platen area of contact is not lubricated, and Breast implant #2 is a single-lumen gel-filled breast implant in which the breast implant-platen area of contact is not lubricated.

These load-displacement measurements can be used to calculate all other breast implant geometric properties as well as engineering stresses, engineering strains and engineering moduli. FIG. 4 also illustrates that the load (F)-plate spacing (H) measurements may be taken manually or automatically by a data acquisition system integrated with the load frame apparatus. The manual (e.g., static) and automatic (e.g., dynamic) measurements on the same breast implant in FIG. 4 also illustrate an important novel feature of this invention, whereby an assumption of quasi-equilibrium can be applied accurately when measuring the load F and geometry of a compressed breast implant. This assumption of quasi-equilibrium is validated as shown in FIG. 4 by the close agreement between the manual, or static, measurements, whereby a load is applied in a stepwise and discrete method, allowing a static state of equilibrium to be achieved between each load F and plate spacing H measurement, and the automatic, or dynamic, measurements, whereby a load F is continuously or dynamically applied while recording the plate spacing H. A quasi-equilibrium process is one in which the deviation from equilibrium is infinitesimal, and all the states the breast implant passes through during the transient process may be considered equilibrium states. Therefore, the quasi-equilibrium assumption approximates all breast implant properties to be constants for every instantaneous compression load during the dynamic, or automatic, load-displacement test process or load program. These breast implant properties include the breast implant diameter D, breast implant H, breast implant surface area A, contact diameter d of the breast implant with the upper and lower plates, contact area of the breast implant with the upper and lower plates, and overall breast implant shape.

Second Invention Embodiment

Figure 5:
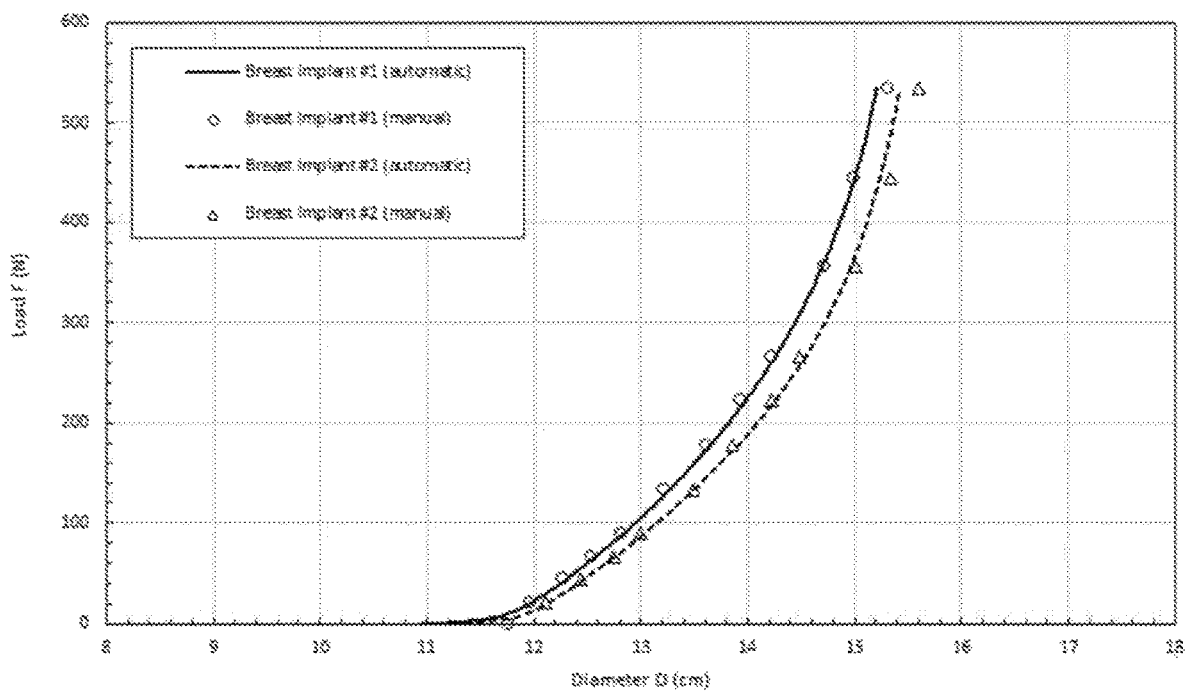
FIG. 5 compares the automatic (dynamic) breast implant diameter to manually (statically) measured breast implant diameter for two breast implants undergoing compression in a load frame apparatus.

FIG. 5 also illustrates how this invention can be accurately applied to calculate the breast implant diameter D from Equation 4 as a function of load F using the plate spacing H data generated while implementing a dynamic load program. FIG. 5 also illustrates that a quasi-equilibrium assumption is valid, and that Equation 4 accurately represents the geometry of a compressed breast implant by comparing the manually measured breast implant diameter D to the computed breast implant diameter D. The manual, or static, measurements of D are taken at discrete loads, whereby the load frame is paused and manual measurements for D are taken. The automatic, or dynamic, values for D are determined from the dynamic data for plate spacing with a geometric model and quasi-equilibrium assumption as in Equation 4. In FIG. 5, Breast implant #1 is a gel-filled single-lumen breast implant in which the breast implant-platen area of contact is not lubricated, and Breast implant #2 is a another single-lumen gel-filled breast implant in which the breast implant-platen area of contact is not lubricated.

Figure 6:
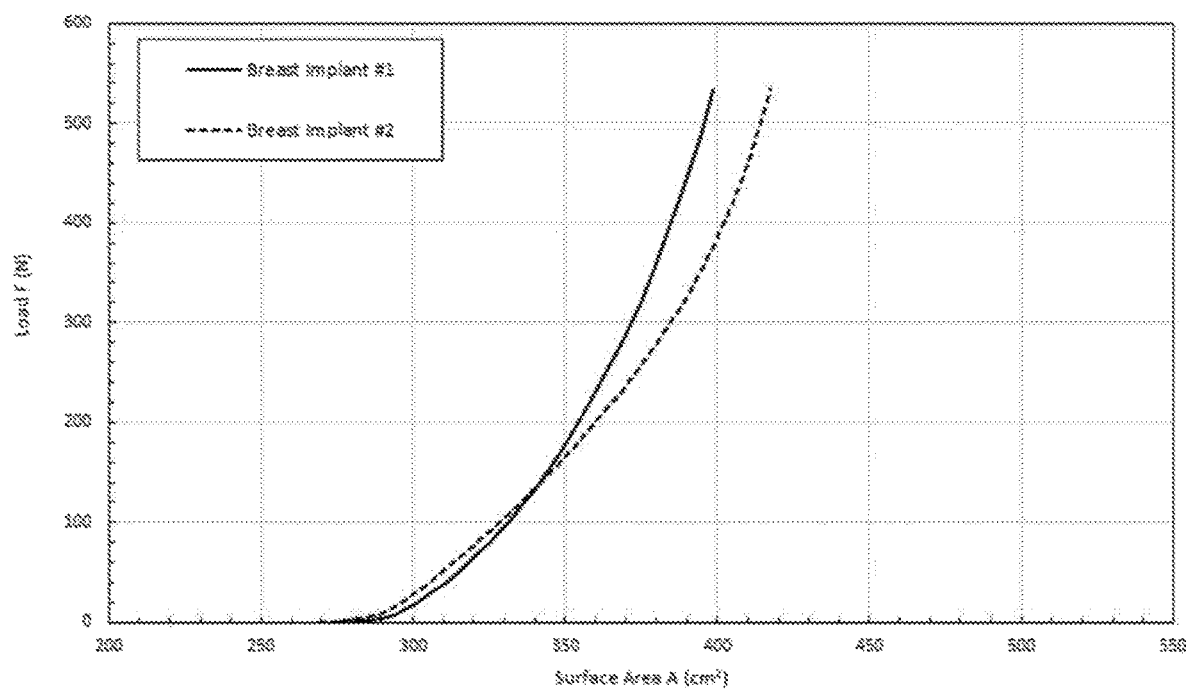
FIG. 6 illustrates the computed surface areas for two breast implants undergoing dynamic compression in a load frame apparatus.

FIG. 6 further illustrates that this invention can be used to determine the breast implant surface area A, which is a function of the plate spacing H (measured dynamically during implementation of a load program) when substituting Equation 4 for the breast implant diameter D into Equation 5. In FIG. 6, Breast implant #1 is a saline-filled dual-lumen breast implant in which the breast implant-platen area of contact is not lubricated, and Breast implant #2 is a single-lumen gel-filled breast implant in which the breast implant-platen area of contact is not lubricated.

Third Invention Embodiment

Figure 7:
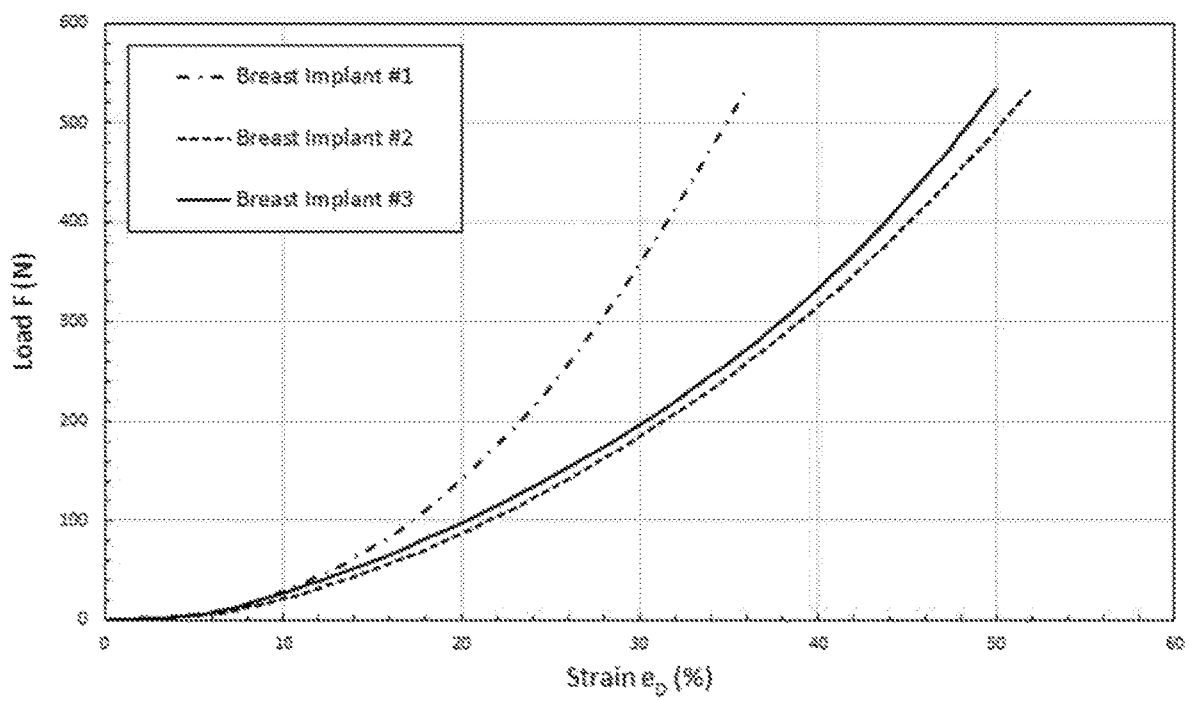
FIG. 7 illustrates the diametric strain for three breast implants as a function of load.

Using only the load (F)-displacement (H) data that is automatically sampled and recorded from a load frame apparatus while implementing a dynamic load program, various engineering strains can be calculated. FIG. 7 illustrates the diametric strain calculated from Equation 9 and dynamic load frame measurements, where the geometric property g is the breast implant diameter D, as a function of load F. The strain in FIG. 7 is expressed as a percentage, which is Equation 9 multiplied by 100%. Similarly, other strains for breast implant height H and breast implant surface area A can be computed. Given a breast implant's volume V (a constant), all strains can therefore be computed using the plate spacing H of the load frame apparatus through Equations 4 and 5. In FIG. 7, Breast implant #1 is a dual-lumen saline-filled breast implant in which the breast implant-platen area of contact is lubricated, Breast implant #2 is a gel-filled single-lumen breast implant in which the breast implant-platen area of contact is lubricated, and Breast implant #3 is another gel-filled single-lumen breast implant in which the breast implant-platen area of contact is lubricated.

Fourth Invention Embodiment

Figure 8:
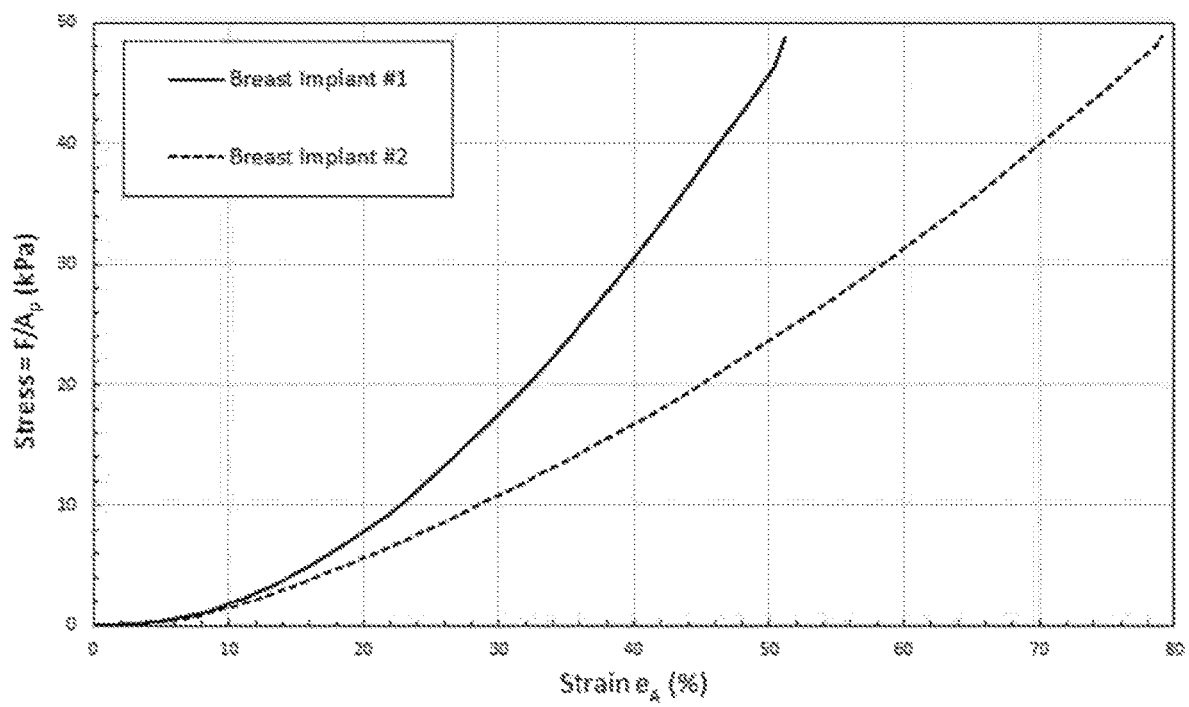
FIG. 8 illustrates stress vs. strain curves for two breast implants generated using the methods of this invention.

FIG. 8 illustrates that engineering stresses can be calculated using the load (F)-displacement (H) data that is automatically sampled and recorded from a load frame apparatus while implementing a dynamic load program. The stress shown in FIG. 8 is the planform stress which is defined as the load divided by the planform area $A_p = \pi D^2/4$, where D is the breast implant diameter. This corresponds to Equation 6, whereby the planform area $A_p$ is used for $A_x$. Other stresses, including but not limited to, circumferential and normal stress, can also be calculated by this invention using the load F and plate spacing H data. In FIG. 8, Breast implant #1 is a dual-lumen saline-filled breast implant in which the breast implant-platen area of contact is lubricated, and Breast implant #2 is a gel-filled single-lumen breast implant in which the breast implant-platen area of contact is lubricated.

Fifth Invention Embodiment

Figure 9:
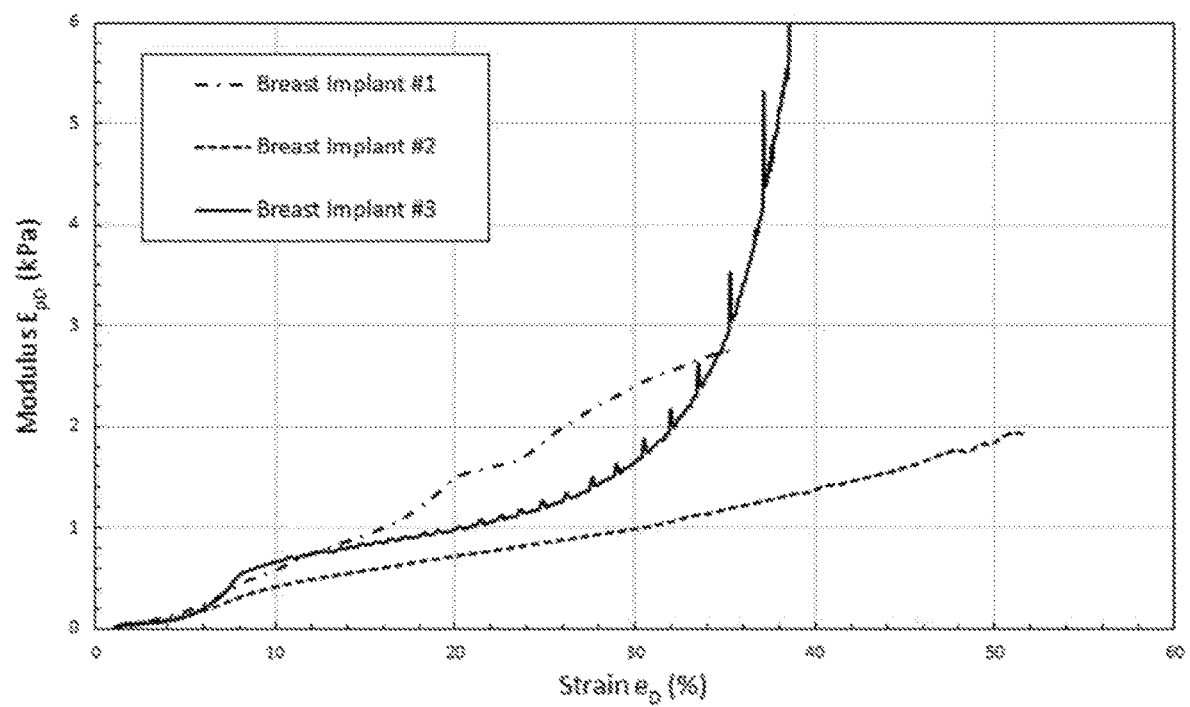
FIG. 9 illustrates engineering moduli for three breast implants calculated using the method of this invention.

Engineering moduli can also be determined using this invention. As shown in FIG. 9, an engineering modulus $E_{pD}$ based on the planform area stress $S_p$ and diametric strain $e_D$ is plotted. The diametric strain is expressed as a percentage in FIG. 9, or Equation 9 multiplied by 100%. This modulus is defined as a tangent modulus, since it is the slope of the stress-strain curve. This particular modulus describes the shape stability of a breast implant, or its resistance to changing shape. The higher the modulus value, the higher the shape stability under compression. Other more traditional moduli are defined as the linear portion of a stress-strain curve as the stress and strain approach zero. This invention provides the means to determine all engineering moduli using only the load F and plate spacing H data from a load frame apparatus given a breast implant's constant volume V. In FIG. 9, Breast implant #1 is a dual-lumen saline-filled breast implant in which the breast implant-platen area of contact is lubricated, Breast implant #2 is a gel-filled single-lumen breast implant in which the breast implant-platen area of contact is lubricated, and Breast implant #3 is another gel-filled single-lumen breast implant in which the breast implant-platen area of contact is not lubricated.

Additional Embodiments

Although this invention is described in terms of breast implants, this invention may also be applied to determine the geometric and engineering mechanical properties of other elastomeric devices undergoing compression. It is also contemplated that this invention can be utilized during the design, development, production, or quality testing of other devices comprised of a monolithic or contiguous elastomeric matrix (i.e., devices that do not have a distinct enclosing shell), or devices comprised of an enclosing thin or thick-walled elastomeric shell filled with a fluid or gel.

It is further contemplated that an elastomeric device may be comprised of a multi-lumen structure of at least two shell-enclosed lumens, whereby each of the at least two shell-enclosed lumens is filled with a fluid or gel. For example, for dual-lumen breast implant devices, the two shell-enclosed lumens are typically "nested," with one shell-enclosed lumen contained within the lumen of, and sharing a common axis with, a second shell-enclosed lumen. There are breast implants comprised of dual lumen saline-filled silicone shells, breast implants having two lumens enclosed by shells having one lumen filled with silicone-gel and the other saline, and breast implants having two lumens each enclosed by silicone shells with one lumen filled with a fluid such as air and the other lumen filled with silicone gel or saline. This invention can be used to determine the geometric properties as well as the engineering stresses, engineering strains and engineering moduli for each of the shell-enclosed lumens comprising the multi-lumen elastomeric device or multi-lumen breast implant using quasi-equilibrium geometric models and engineering mechanical models such as Equations 1-10, wherein each shell-enclosed lumen can be characterized by a volume and shell thickness and separate geometric models. This invention can also be used to determine the overall geometric properties, engineering stresses, engineering strains and engineering moduli of a multi-lumen elastomeric device or breast implant when using the total volume (i.e., the volume of all shell-enclosed lumens comprising the elastomeric device or breast implant) of the multi-lumen elastomeric device or breast implant with quasi-equilibrium geometric models such as Equations 1-10.

It is also contemplated that this invention can be used as part of cyclic fatigue and ultimate strength testing of elastomeric devices to provide the elastomeric device designer a thorough understanding of the stresses and strains endured by the elastomeric device. During cyclic fatigue testing, elastomeric devices (e.g., breast implants) are cycled between two compressive loads with a frequency, in which one of the compressive loads could be zero or near-zero. Typically, cyclic fatigue load frequencies used for fatigue testing ranges from about 1 Hz to about 10 Hz, however this method could be used with any cyclic load frequency achievable by the load frame apparatus.

A range of crosshead speeds may be used with this invention since the quasi-equilibrium assumption coupled with an appropriate geometric model for a compressed breast implant was discovered to be valid. For automated, or dynamic, load frame testing, typical crosshead speeds that can be used for this invention range from about 0.005 cm/min to about 100 cm/min, with preferred crosshead speeds ranging from about 2.5 cm/min to about 50 cm/min.

As a breast implant is dynamically compressed by a load frame apparatus using the method of this invention, the compressive load and plate spacing are recorded at a sampling rate programmed by the data acquisition system integrated with the load frame apparatus. Preferred sampling rates for this invention are about 1 to about 1000 samples per second.

The force, or load, range utilized by this invention for a breast implant should correspond to those compressive forces typically encountered in vivo. Typical in vivo forces on breast implants can reach about 1000 N, although higher forces may be possible during less common events such as automobile accidents or falling from a height.

It is also contemplated that upper plate, lower plate or both upper and lower plate can have a surface that is contoured (for example, to simulate the curvature of a human chest wall in the case of a breast implant.)

It is further contemplated that a software program may be integrated into the load frame apparatus electronics and data acquisition system to provide conversion of the load-displacement raw data directly to breast implant geometric properties and engineering mechanical properties using an appropriate quasi-equilibrium geometric model for the compressed breast implant.

When breast implants are inside the breast capsule, they are surrounded by synovial fluid which can provide a varying degree of lubrication at the breast implant-breast capsule interface. The degree of lubrication within a breast capsule can also vary by a person's specific physiology and the viscosity of the synovial fluid surrounding the breast implant in a breast capsule. Therefore, a preferred embodiment of this method is to test breast implants both with and without a lubricated interface between the breast implant and platens. Lubrication consists of applying a layer of aqueous solution, silicone oil or other lubricating fluid at the contact area interface between the load frame apparatus platens and the breast implant. Breast implants can also be tested using lubricants having a viscosity range expected to simulate the viscosity range of synovial fluid in a breast capsule, or by using synthetic synovial fluid. Testing breast implants with both lubricated and unlubricated interfaces with the load frame apparatus platens ensures that the engineering stresses, strains and moduli are characterized over the full spectrum of possible in vivo environments. In fact, during the development of this invention, it was discovered that the engineering stresses, strains, and moduli with lubricated and unlubricated breast implant-platen interfaces may be different.

It is also contemplated that this invention can be used to characterize the engineering mechanical properties of anatomically shaped breast implants, since although anatomically shaped breast implants are not symmetric in a zero-load state, these implants will deform to a flattened cylinder and the outer-half of a torus geometry when subjected to a compressive load between the two platens of a load frame apparatus.

The preferred platens comprising the load frame apparatus should be constructed of a rigid material including, but not limited to, stainless steel, aluminum, and high strength plastics. Preferably, the surface roughness for the platens should be in the "polished" category, having a surface roughness on the order of about 1 micrometer or less.

For implementation of this invention, it is also preferred that the lubricant, degree of lubrication, platen material and platen surface finish is consistent, especially when comparing the engineering mechanical properties of breast implants (or other elastomeric devices) from different manufacturers.

It is further contemplated that elastomeric devices having substantially spherical geometry, cylindrical geometry, elliptical geometry or combinations thereof can be described geometrically in terms of the plate spacing of a load frame apparatus when compressed, thereby allowing this invention to be applied to compute engineering stresses, engineering strains and engineering moduli from a load frame apparatus load-displacement data.

The elastomeric devices and breast implants that can be tested using the methods of this invention are comprised of materials including, but not limited to, silicone, polyurethane, polyester, polyether, polystyrene, neoprene, polyisoprene, polypropylene oxide, natural rubber, hydrogels, and composites or co-polymers thereof. For medical devices such as breast implants, the preferred materials should be biocompatible.

Although this invention has been described in specific detail with reference to the enclosed detailed description and invention embodiments, it will be understood that many variants, modifications and combinations of the invention embodiments may be effected within the spirit and scope of the invention as described in the appended claims.

The invention claimed is:

1. A method for determining the geometric properties and engineering mechanical properties of a breast implant using a load frame apparatus, the load frame apparatus comprising an upper plate and a lower plate, the breast implant having a breast implant volume and breast implant shell thickness, the method comprising the steps of:

Loading the breast implant into said load frame apparatus, wherein said breast implant is disposed between said upper plate and said lower plate;

Implementing a dynamic load frame apparatus program wherein said upper plate and said lower plate form an area of contact with said breast implant, wherein the separation distance between said upper plate and said lower plate is plate spacing, wherein a dynamic compressive load is applied to said breast implant by a dynamic change in plate spacing, and wherein said plate spacing has a rate of change that is crosshead speed;

Recording said dynamic compressive load and said plate spacing at a sampling rate;

Providing a quasi-equilibrium geometric model for said breast implant that is entirely a function of said plate spacing and said breast implant volume;

Computing the breast implant geometric properties from said quasi-equilibrium geometric model; and Computing said engineering mechanical properties from said breast implant geometric properties, said breast implant shell thickness, and said dynamic compressive load.

2. The method of claim 1, wherein said dynamic load frame apparatus program is selected from the group consisting of an increasing compressive load, an oscillatory compressive load further comprising a frequency, a decreasing compressive load, and combinations thereof.

3. The method of claim 1, wherein said geometric model is a composite of a flattened cylinder and outer-half of a torus.

4. The method of claim 1, wherein said engineering mechanical properties comprise at least one of engineering stresses, engineering strains or engineering moduli.

5. The method of claim 1, wherein said breast implant geometric properties are breast implant diameter D, breast implant surface area A, and breast implant contact diameter d with said upper plate and said lower plate.

6. The method of claim 1, wherein said quasi-equilibrium geometric model includes breast implant diameter D, breast implant surface area A, said plate spacing H, and said breast implant volume V given by $$D = H + \frac{1}{2}\left(-\frac{\pi}{2}H + \sqrt{\frac{16}{\pi}\frac{V}{H} + \left(\frac{\pi^2}{4} - \frac{8}{3}\right)H^2}\right)$$

$$A = \frac{\pi}{2}D^2 + \left(\frac{\pi^2}{2} + \pi\right)DH + \left(\frac{3\pi}{2} - \frac{\pi^2}{2}\right)H^2$$

7. The method of claim 1, wherein said area of contact is lubricated.

8. The method of claim 1, wherein said upper plate and said lower plate have a surface roughness on the order of about 1 micrometer or less.

9. The method of claim 1, wherein the said upper plate and said lower plate have surfaces that are parallel.

10. The method of claim 1, wherein said sampling rate ranges from about 1 to about 1000 samples per second.

11. The method of claim 1, wherein said crosshead speed ranges from about 0.005 cm/min to about 100 cm/min.

12. The method of claim 1, wherein said breast implant is an anatomically shaped breast implant.

13. The method of claim 2, wherein said frequency ranges from about 1 Hz to 10 Hz.

14. The method of claim 4, wherein said engineering stresses are selected from the group consisting of planform, circumferential and normal.

15. The method of claim 4, wherein said engineering strains are selected from the group consisting of projection, diametric and areal.

16. A method for determining the geometric properties and engineering mechanical properties of a multi-lumen breast implant using a load frame apparatus, the load frame apparatus comprising an upper plate and a lower plate, the multi-lumen breast implant comprising at least two shell-enclosed lumens wherein each of the at least two shell-enclosed lumens has a volume and shell thickness, the method comprising the steps of:

Loading the breast implant into said load frame apparatus, wherein said multi-lumen breast implant is disposed between said upper plate and said lower plate;

Implementing a dynamic load frame apparatus program wherein said upper plate and said lower plate form an area of contact with said multi-lumen breast implant, wherein the separation distance between said upper plate and said lower plate is plate spacing, wherein a dynamic compressive load is applied to said multi-lumen breast implant by a dynamic change in plate spacing, and wherein said plate spacing has a rate of change that is a crosshead speed;

Recording said dynamic compressive load and plate spacing at a sampling rate;

Providing a quasi-equilibrium geometric model for said multi-lumen breast implant that is a function of said plate spacing;

Computing the multi-lumen breast implant geometric properties from said quasi-equilibrium geometric model; and Computing said engineering mechanical properties from said multi-lumen breast implant geometric properties.

17. The method of claim 16, wherein said dynamic load frame apparatus program is selected from the group consisting of an increasing compressive load, an oscillatory compressive load further comprising a frequency, a decreasing compressive load, and combinations thereof.

18. The method of claim 16, wherein said area of contact is lubricated.

19. The method of claim 16, wherein said quasi-equilibrium geometric model further comprises separate quasi-equilibrium geometric models for each of the at least two shell-enclosed lumens.

20. A method for determining the geometric properties and engineering mechanical properties of an elastomeric device using a load frame apparatus, the load frame apparatus comprising an upper plate and a lower plate, the elastomeric device having an elastomeric device volume, the method comprising the steps of:

Loading the elastomeric device into said load frame apparatus, wherein said elastomeric device is disposed between said upper plate and said lower plate;

Implementing a dynamic load frame apparatus program wherein said upper plate and said lower plate form an area of contact with said elastomeric device, wherein the separation distance between said upper plate and said lower plate is plate spacing, wherein a dynamic compressive load is applied to said elastomeric device by a dynamic change in plate spacing, and wherein said plate spacing has a rate of change that is crosshead speed;

Recording said dynamic compressive load and said plate spacing at a sampling rate;

Providing a quasi-equilibrium geometric model for said elastomeric device that is a function of said plate spacing and said elastomeric device volume;

Computing the elastomeric device geometric properties from said quasi-equilibrium geometric model; and Computing said engineering mechanical properties from said elastomeric device geometric properties and said dynamic compressive load.

\* \* \* \* \*